United States Patent
Brossette et al.

(10) Patent No.: US 6,571,198 B1
(45) Date of Patent: May 27, 2003

(54) METHOD FOR ANALYZING SETS OF TEMPORAL DATA

(75) Inventors: Stephen E. Brossette, Birmingham, AL (US); Stephen A. Moser, Mountain Brook, AL (US); Alan P. Sprague, Columbus, OH (US); Michael J. Hardin, Alabaster, AL (US); Warren T. Jones, Birmingham, AL (US)

(73) Assignee: UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/554,359

(22) PCT Filed: Nov. 12, 1998

(86) PCT No.: PCT/US98/24096

§ 371 (c)(1),
(2), (4) Date: Jul. 10, 2000

(87) PCT Pub. No.: WO99/24912

PCT Pub. Date: May 20, 1999

(51) Int. Cl.[7] ............................................. G06F 15/177
(52) U.S. Cl. ............................ 702/179; 707/6; 707/200
(58) Field of Search ........................... 702/179; 707/216, 707/200, 102; 706/50, 45; 709/242, 244; 345/841, 864

(56) References Cited

U.S. PATENT DOCUMENTS

| 5,440,738 A | | 8/1995 | Bowman et al. ............. 707/6 |
|---|---|---|---|
| 5,590,325 A | | 12/1996 | Kolton et al. ............. 707/6 |
| 5,893,910 A | * | 4/1999 | Martineau et al. ............ 707/10 |
| 6,105,025 A | * | 8/2000 | Jacobs et al. ............. 707/8 |
| 6,192,358 B1 | * | 2/2001 | Fuh et al. ............. 707/4 |
| 6,253,196 B1 | * | 6/2001 | Fuh et al. ............. 707/3 |
| 6,389,425 B1 | * | 5/2002 | DeMichiel et al. ......... 707/102 |
| 6,393,409 B2 | * | 5/2002 | Young et al. ............. 705/37 |

* cited by examiner

Primary Examiner—Kamini Shah
(74) Attorney, Agent, or Firm—Gifford, Krass, Groh, Sprinkle, Anderson & Citkowski, P.C.

(57) ABSTRACT

A method for analyzing sets of temporal data using a computer wherein each set of temporal data includes a plurality of records collected at a time unique to each such set and in which each record has a plurality of data items. The method includes the first step of creating data association rules for at least a plurality of sequential sets wherein each association rule represents data records having at least some common data items (100). A confidence factor is then determined for each such association rule and these confidence factors are stored in data partitions for the temporal data sets (102). The confidence factors for a selected data partition is then compared with the corresponding confidence factors of at least one other data partition (112), if available. When the confidence factor for the selected data partition varies from the corresponding confidence factor for the at least one other data partition exceeds a threshold value, an alert output signal is generated (114).

4 Claims, 2 Drawing Sheets

METHOD FOR ANALYZING SETS OF TEMPORAL DATA

BACKGROUND OF THE INVENTION

I. Field of the Invention

The present invention relates generally to a data analysis computer program and, more particularly, to a data analysis program for analyzing sets of temporal data such as temporal health care surveillance data, and especially epidemiological data.

II. Description of the Prior Art

There are many health care databases, e.g. epidemiology databases, containing temporal data, i.e. data which is collected at periodic time intervals. Such databases, furthermore, typically include bacterial antimicrobial data, resistance data and the like at hospital, regional and national levels. Domain experts in epidemiology and laboratory medicine currently review the antimicrobial susceptibility data at half year, yearly or even longer intervals in an effort to discover significant new patterns, information and trends of the data. This time deferred and late discovery of such trends results in increased inefficiency and increased cost of treatment in the medical field.

Additionally, at present domain experts perform only manual analysis of the data in an effort to discover trends and patterns of health care or epidemiological data. Such manual analysis includes database queries and confirmatory statistics to specific questions in an effort to test specific hypotheses. These traditional methods of data analysis, however, offer no way to discover patterns and trends that are not suspected by the investigators of the data. Consequently, such unsuspected trends and patterns are simply ignored and remain undiscovered even though such trends and patterns may be significant.

SUMMARY OF THE PRESENT INVENTION

The present invention provides a method for analyzing sets of temporal data, especially epidemiological data, which automatically identifies significant trends and patterns in the data and does so in a timely fashion.

In brief, the method of the present invention analyzes sets of temporal data wherein each set of temporal data comprises a plurality of records collected at a time period unique to each such set. Each record has a plurality of data items including, for example, patient characteristics, the organism isolated, source of the sample, date reported, location of patient and one or more antimicrobials used to test the sample against.

The method of the present invention includes the first step of creating data association rules for at least a plurality of sequential data sets, i.e. sequential temporal data sets, wherein each such data set includes at least some common data items. Each association rule is only considered if it has precondition support in some predetermined number of records. Otherwise, the association rule is discarded as statistically insignificant.

After determining the data association rules, the confidence factor for each such association rule is determined where the confidence factor for the association rule $A \rightarrow B$ represents the likelihood or probability of B given A.

For example, given a data item A and a data item B where the intersection of A and B is empty, the confidence factor Conf(R, P) where rule $R=(A \rightarrow B)$ in partition P, Conf(R, P), is $S(A \cup B)/S(A)$ where $S(X)$ is the Support of X in P. Such association rules, together with the confidence factor for each such rule, is stored in a history.

In order to determine significant patterns or trends over time, the association rule and confidence factors for the current data set are first determined. The confidence factors for each association rule are then compared with the confidence factors for the corresponding association rule, if present in the history, from previous data partitions. A change in confidence of a particular association rule, such that the probability that the change occurred by chance is less than some predefined percentage (e.g. 5%) as determined by a chi-square test of two proportions or some other applicable statistical test, generates an alert signal to the operator. Following analysis of all of the data in the current data set, the alert signals are displayed or otherwise conveyed to the operator user who then takes whatever action is appropriate.

In the preferred embodiment of the invention, the alerts are clustered into events prior to displaying such alerts to the operator. Such alert clustering groups descendant association rules with the parent association rule into an event. An association rule $A1 \rightarrow B1$ is defined as a dependent of association rule $A2 \rightarrow B2$ if the set of items in A2 is contained in A1 and, likewise, $B2 \subseteq B1$. Dependent also contains that a descendent association rule accounts for the change detected in the parent association rule.

A primary advantage of the present invention is that it rapidly identifies related clusters of high support association rules whose confidences change significantly over time. Using traditional methods, these clusters might be overlooked.

BRIEF DESCRIPTION OF THE DRAWING

A better understanding of the present invention will be had upon reference to the following detailed description when read in conjunction with the accompanying drawing, wherein like reference characters refer to like parts throughout the several views, and in which.

DETAILED DESCRIPTION OF A PREFERRED EMBODIMENT OF THE PRESENT INVENTION

Figure 1:
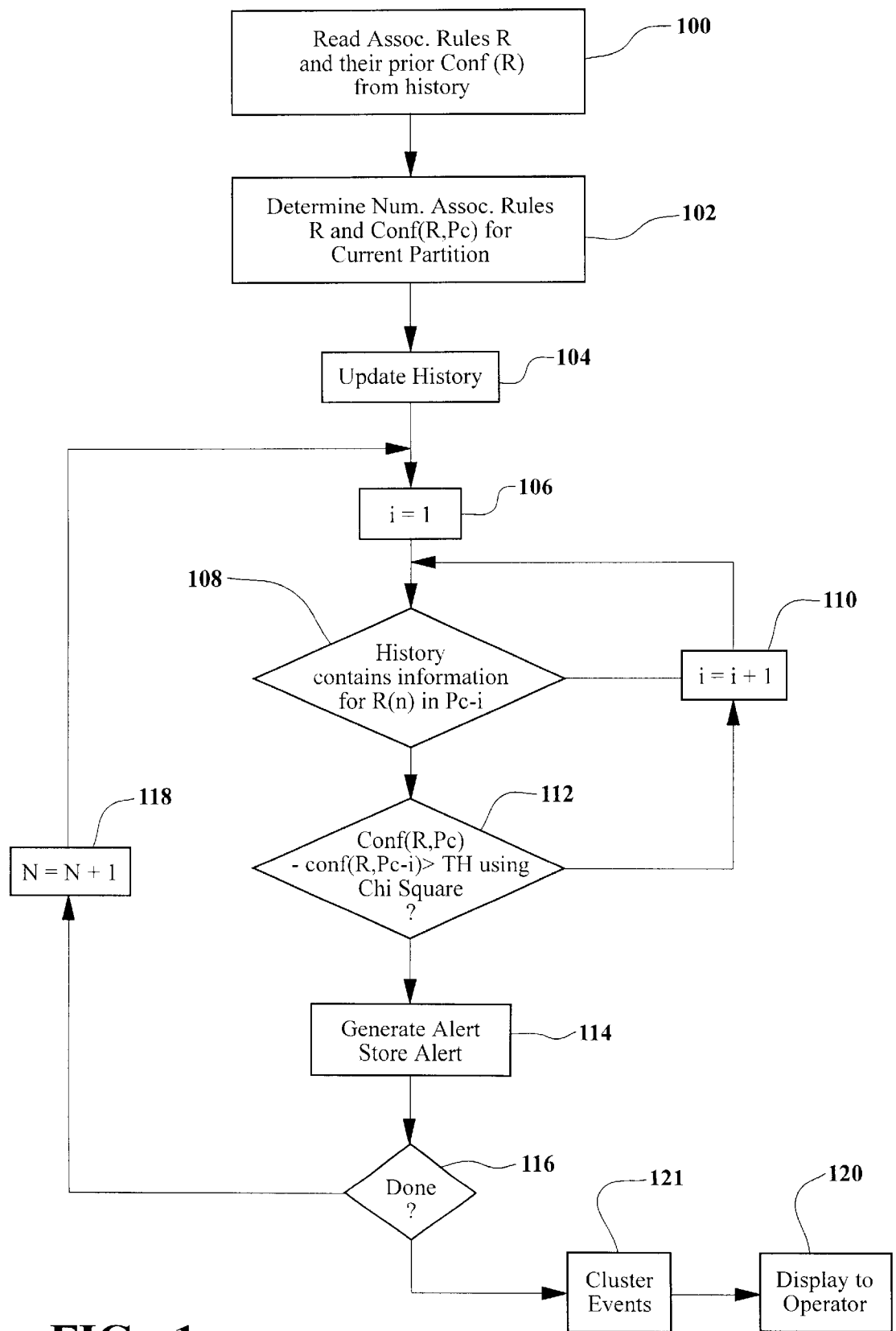
FIG. 1 is a flow chart illustrating a portion of the preferred embodiment of the present invention.

Temporal or time slice health care data is typically collected in data sets, each data set P representing a plurality of individual records where n represents the particular data set. Each individual record, in turn contains data items a, b, c etc. The individual data items, however, are mutually exclusive of each other. Frequent sets A,B, each containing sets of items are also defined. For example frequent set A may contain items a, b and c while frequent set B may contain items d, e and f. Thus, an item X cannot be in both frequent sets A and B for a given rule $A \rightarrow B$.

Using conventional methods, association rules, e.g. $R=A \rightarrow B$, are then determined for all of the data records in the data partition P that optionally initially pass user defined rule templates. Such association rules R, however, are only considered when there is sufficient support, i.e. the items of A are found together in a sufficient number of data records, in a particular data set P. Otherwise, the association rule is simply discarded as being statistically insignificant.

Once the association rules have been determined for the data set $P_C$, a confidence factor Conf(R, $P_C$) is then determined for each association rule R in the data partition $P_C$.

For example, assuming association rule R=A→B has sufficient support in P, if the items in B occur in 60% of the data records of P that the items of A occur in, then the probability of B given A, Conf(R, P), is 60%.

Any conventional means may be utilized to identify the association rules, ensure that the association rules have sufficient support to have statistical interest as well as to calculate the confidence factor Conf(R, P) for each association rule R in the entire data set P.

According to the present invention and as will be shortly described in greater detail, the confidence factors Conf(R, $P_C$) of the current data set $P_C$ are then compared with the corresponding confidence factors Conf(R, $P_{C-i}$) for previous data sets, if such association rule is present in the previous data sets. When the change in the confidence factor for a particular association rule(s) exceeds a predetermined threshold, e.g. 5% variation as determined by a chi-square test of two proportions or some other applicable statistical test, an alert signal is created and stored. Following the analysis of all of the data in the current data set $P_C$, the alert signals generated by the comparison of the confidence factors is then displayed to the operator. Furthermore, the alert signals are preferably clustered into events of ancestor and descendent association rules where a descent association rule A2→B2 is a descendent of the association rule A1→B1 if the set of items A2 is contained in A1 and, likewise, B2⊆B1. Dependent also contains that a descendent association rule accounts for the change detected in the parent association rule. Such clustering of related ancestor and descendent association rules into events enables more efficient data analysis by the operator.

With reference now to FIG. 1, analysis of the data items in the current data set $P_C$(C=current) is compared with the association rules and confidence factors in prior data sets $P_{C-1}$, $P_{C-2}$, $P_{C-3}$ . . . is there shown. At step 100, the association rules R and confidence factors Conf(R, $P_{C-i}$) are first read from the history where i equals a counter for the prior data sets. The history is conventionally stored on magnetic media of any conventional type.

At step 102 the association rules R as well as the confidence factors Conf(R, $P_C$) are then determined for the data contained in the current data set or current partition $P_C$. Step 102 then exits to step 104 which updates the history for the current data set $P_C$.

Step 104 then branches to step 106 which sets the variable i equal to 1. The variable i is used, as will become shortly evidence, to iterate through the association rules and confidence factors in prior partitions. Step 106 then branches to step 108.

Assuming that there are n association rules R having sufficient support in the current data set $P_C$, step 108 then identifies the first association rule $R_1$ ($R_n$ where n=1) in the current data set $P_C$ and determines if the association rule $R_1$ was identified in the prior partition $P_{C-i}$. If not, step 108 branches to step 110 which increments the value of i and then branches back to step 108. Consequently, the loop represented by step 108 and step 110 iteratively searches the confidences of association rule $R_1$ for all of the previous partitions $P_{C-i}$.

Conversely, assuming that the association rule $R_1$, i.e. the first association rule in the current data set $P_C$ is also present in the data partition $P_{C-i}$, step 108 instead branches to step 112 in which the change of the confidence factor for the association rule $R_1$ in the current data set $P_C$, Conf($R_1$, $P_C$) with the corresponding confidence factor in the earlier data set P Conf($R_1$, $P_{C-i}$) is greater than a predetermined threshold $T_H$ as determined by a chi-square test of two proportions. If not, step 112 then branches to step 110 which increments the counter i for the data set $P_{C-i}$ and then returns to step 108.

Conversely, if the confidence factor for the association rule $R_1$ has changed more than the threshold amount $T_H$ as determined by a chi-square test of two proportions, step 112 instead branches to step 114 which both generates and stores an alert. Step 114 then branches to step 116 which determines if all of the rules $R_i$ in the current data set $P_C$ have been analyzed in the previously described fashion. If not, step 116 branches to step 118 which increments the counter n to the next association rule $R_n$. Step 118 then branches to step 106 where the above-identified process is repeated.

As can thus be seen, with the iterative algorithm depicted in FIG. 1, the confidence factor Conf($R_n$, $P_C$) for each association rule $R_n$ in the current set $P_C$ is compared with the confidence factor Conf($R_n$, $P_{C-i}$) for the corresponding association rule in the previous data sets $P_{C-i}$. If the confidence factor changes by more than a preset threshold $T_H$ as determined by a chi-square test of two proportions, an appropriate alarm is generated.

Following complete analysis of all of the data in the current data set $P_C$, step 116 branches to step 120 which presents the results to the operator.

Figure 2:
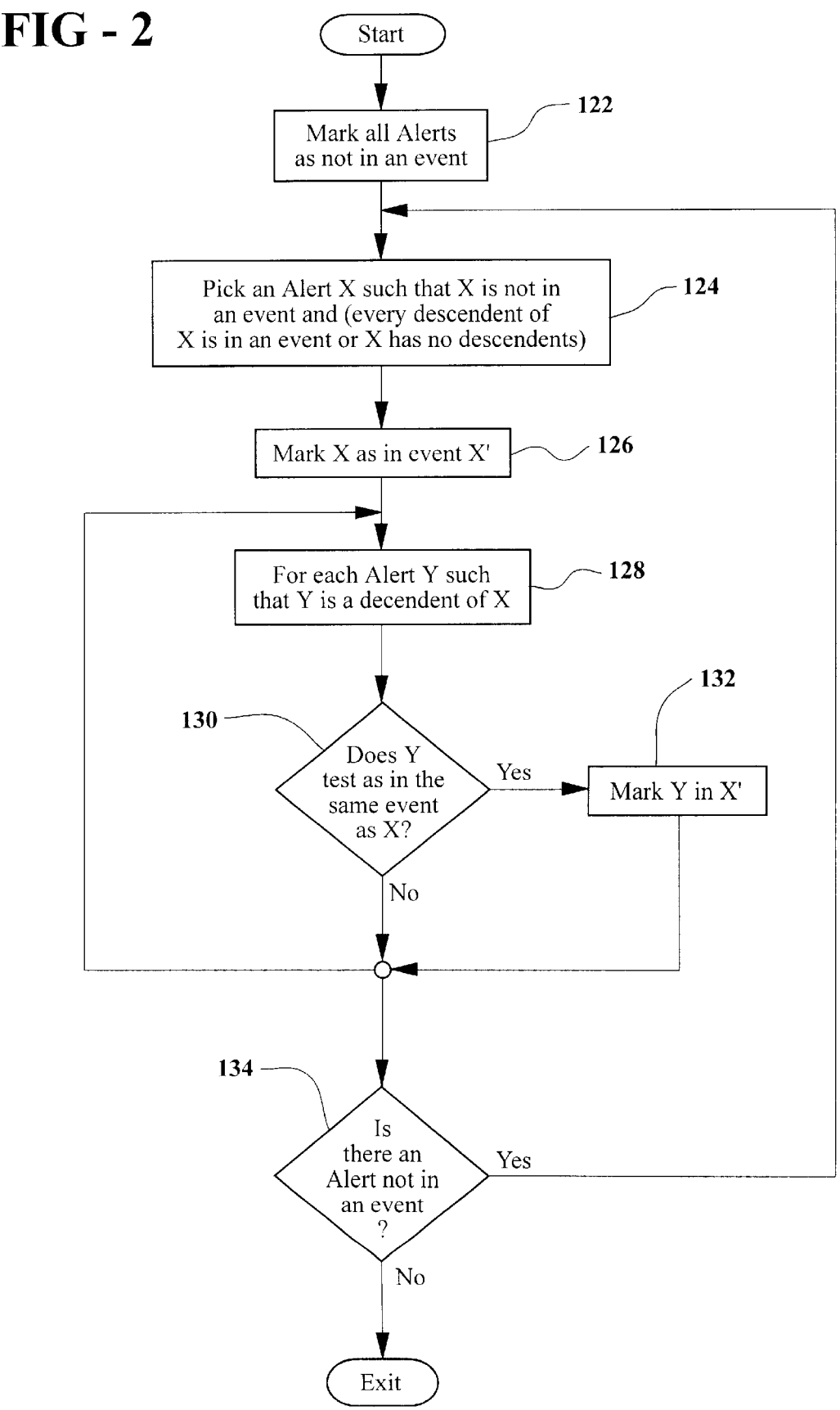
FIG. 2 is a flow chart illustrating another portion of the preferred embodiment of the present invention.

With reference now to FIG. 2, in order to provide more efficient data analysis of the alerts generated at step 114 (FIG. 1) the alerts are clustered. As best shown in step 122, all of the alerts generated at step 114 (FIG. 1) are first marked as not in an event. Step 122 then branches to step 124. At step 124 an alert X is selected such that the alert X is not in an event and that every descendent of X is in an event or that X has no descendants. Step 124 then branches to step 126. Step 126 then marks X as an event X' and then branches to step 128. Step 128 then identifies each alert Y that is a descendent of X and then branches to step 130.

Step 130 then determines if Y is in the same event as X. If so, step 130 branches to step 132 which marks alert Y as in event X'. Otherwise, step 130 increments the alert Y and then branches back to step 128 where the above process is repeated.

After each alert Y has been examined for the first selected alert X, step 132 branches to step 134 which tests that there is an alert that is not in an event. If so, step 134 branches to step 124 where the above-identified process is repeated. Otherwise, step 134 exists to step 120 (FIG. 1).

From the foregoing, it can be seen that the present invention provides a novel method of analyzing temporal data such as the type of data used in health surveillance. No unnecessary limitation, however, should be drawn therefrom since the data analysis method of the present invention may be used for any type of temporal data.

A primary advantage of the present invention is that, unlike previous methods which primary analyze data associations having high support levels and thus oftentimes uninteresting, the present invention instead identifies changes in confidence factors of the various identified association rules. Since it is the confidence factor, rather than the gross number of data records, that is monitored, changes in both common association rules as well as less common association rules, are equally identified and presented to the operator as an alert.

Having described my invention, however, many modifications thereto will become apparent to those skilled in the art to which it pertains without deviation from the spirit of the invention as defined by the scope of the appended claims.

We claim:

1. A method for analyzing sets of temporal data, each data set of temporal data comprising a plurality of records collected at a time period unique to each said set, each record having a plurality of data items, said method comprising the steps of:

creating data association rules for at least a plurality of sequential sets, each association rule representing data records having at least some common data items, determining the confidence factor for each such association, storing said association rules and said confidence factors for said at least a plurality of sequential data sets in data partitions, comparing said confidence factors for each association rule a selected data partition with the corresponding confidence factors for at least one other data partition, generating an output signal whenever the change of confidence factor for said selected data set varies from the corresponding confidence factor for said at least one other data set exceeds a selected threshold value.

2. The invention as defined in claim 1 wherein said creating data association rules step further comprises the step of creating said data association rule only when the number of data records having common data elements exceeds a preset number.

3. The invention as defined in claim 1 wherein said data set comprises health care data.

4. The invention as defined in claim 1 and comprising the further step of clustering output signals corresponding to association rules having common data items.

* * * * *

UNITED STATES PATENT AND TRADEMARK OFFICE
CERTIFICATE OF CORRECTION

PATENT NO. : 6,571,198 B1
APPLICATION NO. : 09/554359
DATED : May 27, 2003
INVENTOR(S) : Brossette et al.

Page 1 of 1

It is certified that error appears in the above-identified patent and that said Letters Patent is hereby corrected as shown below:

In the Specification

Please insert the following paragraph directly under the Description section and before the Field of the Invention section:
--GOVERNMENT SUPPORT CLAUSE
This invention was made with government support under grant number U47/CCU411451 awarded by the Centers for Disease Control and Prevention. The government has certain rights in the invention.--

Signed and Sealed this
Twenty-ninth Day of December, 2020

Andrei Iancu
*Director of the United States Patent and Trademark Office*